United States Patent [19]
Comey, III et al.

[11] Patent Number: 5,859,305
[45] Date of Patent: Jan. 12, 1999

[54] METHOD FOR OPTIMIZING HYDROGEN FLUORIDE ALXYLATION AND INCREASING PROCESS SAFETY

[75] Inventors: Kenneth Roy Comey, III, Bellaire; Gerald Verdell Nelson, Nederland, both of Tex.

[73] Assignee: Texaco Inc, White Plains, N.Y.

[21] Appl. No.: 786,981

[22] Filed: Jan. 24, 1997

Related U.S. Application Data

[63] Continuation-in-part of Ser. No. 370,593, Jan. 10, 1995, abandoned.

[51] Int. Cl.[6] .................................. C07C 2/68; C07C 2/70
[52] U.S. Cl. ......................... 585/725; 585/701; 585/721; 585/723
[58] Field of Search ..................................... 585/723, 725, 585/701, 720, 721, 724

[56] References Cited

U.S. PATENT DOCUMENTS

| | | | |
|---|---|---|---|
| 5,073,674 | 12/1991 | Olah ....................................... | 585/725 |
| 5,277,881 | 1/1994 | Patridge, Jr. et al. .................. | 422/241 |

OTHER PUBLICATIONS

Sheckler et al., "HF Mitigation Via The Texaco–UOP HF Additive Technology", 1994 NPRA Annual Meeting, Mar. 20–22, 1994, pp. 1–14.

Ross, "Initial Operaton of the Alkad Process", API Spring Meeting. May 8–10, 1995, pp. 1–14.

"U.S. Refiners Must Increase Alkylation Capacity to Meet Demand", Oil & Gas Journal, Aug. 22, 1994, pp. 49–54.

Rhodes, "New Process Schemes, Retrofits, Fine tune alkylation Capabilities", Oil & Gas Journal, Aug. 22, 1994, pp. 56–59.

Williams et al., "Alkad Operations at Texaco's El Dorado Plant", 1995 NPRA Annual Meeting, Mar. 19–21, 1995, pp. 1–12.

"Chementator", Chemical Engineering, Dec. 1994, p. 21.

Sheckler, et al., "New Process Additive Reduces HF Cloud–Forming Potential", Oil & Gas Journal, Aug. 22, 1994, pp. 60–63.

"Chementator", Chemical Engineering, Sep. 1995, p. 23.

"Letters", Chemical Engineering, May 1996, p. 8.

"Chementator", Chemical Engineering, Oct. 1995, p. 17.

Schatz et al., "Apparatus for Field Testing of HF Releases", AIChE Summer National Meeting, Aug. 15–18, 1993, pp. 1–14.

Comey III et al., "Aerosol Reduction from Episodic releases of Anhydrous Hydrofluoric Acid by Modifying the Acid Catalyst with Liquid Onium Poly (Hydrogen Fluorides)", AIChE 1993 Summer National Meeting, Aug. 16, 1993, pp. 1–17.

Melhem et al., "the Texaco/UOP HF Alkylation Additive Technology: Aerosolization Reduction Effects", 2nd International Conference and Workshop, Sep. 1995, pp. 1–53.

(List continued on next page.)

*Primary Examiner*—Michael L. Lewis
*Assistant Examiner*—Alexander G. Ghyka
*Attorney, Agent, or Firm*—Henry H. Gibson; Arnold White & Durkee

[57] ABSTRACT

A method of regulating the concentration of onium in a liquid onium poly(hydrogen fluoride) composition utilized in a hydrogen fluoride catalyzed alkylation reaction for a given level of total airborne hydrogen fluoride is disclosed. Also disclosed is a method of regulating the concentration of onium in the liquid onium poly(hydrogen fluoride) composition for a given level of RON. In one embodiment, the liquid onium poly(hydrogen fluoride) composition is a mixture including pyridine and anhydrous hydrogen fluoride so as to give a pyridine poly(hydrogen fluoride) composition that is useful as a catalyst in the hydrogen fluoride catalyzed alkylation reaction.

15 Claims, 1 Drawing Sheet

OTHER PUBLICATIONS

Jersey et al., "Large–Scale Release Testing of a Modified HF Alkylation Catalyst", 1993 AICHE Summer National Meeting, Aug. 15–18, 1993, pp. 1–7.

Dialog Search Nov. 17. 1996.

1981, 1982, 1986 NPRA Question & Answer Session on Refining and Petrochemical Technology no month.

Stevenin, "Hydrofluoric Acid Catalyzed Alkylation", Alkylation for Motor Fuels, Process Economics Program, Feb. 1974, pp. 105–139.

Corma et al., "chemistry, Catalysts, and Processes for Isoparaffin—Olefin Alkylation: Actual Situation and Future Trends", Catal. Rev.—Sci. Eng., 1993, pp. 483–570 no month.

METHOD FOR OPTIMIZING HYDROGEN FLUORIDE ALXYLATION AND INCREASING PROCESS SAFETY

This is a continuation-in-part of application Ser. No. 08/370,593 filed on Jan. 10, 1995 now abandoned.

BACKGROUND OF THE INVENTION

1. Field of the Invention

The present invention is generally directed to a method of regulating the liquid onium poly(hydrogen fluoride) composition utilized in a hydrogen fluoride catalyzed alkylation reaction.

2. Background

The catalytic alkylation of an isoparaffin with an olefin to produce a branched paraffin is a commercially important process for producing high octane gasoline. In general, the process comprises the reaction of an isoparaffin such as isobutane with an olefin such as propylene, 1-butene, 2-butene or mixtures thereof in the presence of a liquid acid alkylation catalyst in a reaction zone. Reaction is followed by separation of the product and unreacted hydrocarbons from the liquid alkylation catalyst in a settling zone and purification of the alkylate product. If the isoparaffin is isobutane and the olefin is a butene, the alkylate product is isooctane. Alkylate product is used to enhance the octane number of automotive gasoline and aviation gasoline.

Strong mineral acids are particularly effective catalysts for this alkylation process. Anhydrous sulfuric and anhydrous hydrofluoric acid (hereafter, HF) are examples of two commonly used acid catalysts. Though effective, the volatility and destructive effect of super-heated, pressurized mineral acids on animal and human tissue are well known. In another study it was shown that a release of HF from an alkylation reactor would form a dense aerosol cloud that could travel several kilometers downwind and only slowly disperses.

One method of mitigating the potential danger of an accidental release of HF has been the development of containment systems that spray water or aqueous neutralizing agent upon the detection of a reactor leak. Such systems rely on detection technology and/or plant personnel to determine if a hazardous condition exists before activation of the spray system.

Another method of mitigating the potential danger of accidental release of HF is the proposed use of HF containing compositions in the HF alkylation reaction that lower the volatility of HF. One such method is disclosed in U.S. Pat. No. 5,073,674 to G. A. Olah in which liquid onium poly (hydrogen fluoride) complexes are suggested as being useful. One skilled in the art, however, should appreciate that actual practice of such a system will require a balance of chemical reactants, reaction conditions and environmental conditions in order to achieve a commercially viable sustained reaction process.

SUMMARY OF THE INVENTION

One aspect of the present invention is generally directed to a method of regulating the formulation of a liquid onium poly(hydrogen fluoride) composition utilized in a hydrogen fluoride catalyzed alkylation reaction for a given level of total airborne hydrogen fluoride reduction. The present method includes determining an ambient temperature value, measuring alkylation reaction temperature and pressure values, determining the actual formulation of the liquid onium poly(hydrogen fluoride) composition, calculating a target concentration value of the onium in the composition using the equation disclosed herein and adjusting the actual concentration value to approximate the target concentration value. In this way a predetermined level of total airborne hydrogen fluoride reduction can be achieved and maintained throughout the alkylation reaction process. In one preferred embodiment of this aspect of the invention, the liquid onium poly(hydrogen fluoride) composition includes pyridine and anhydrous hydrogen fluoride.

Another aspect of the present invention is generally directed to a method of regulating the formulation of the liquid onium poly(hydrogen fluoride) composition for a given level of Research Octane Number (RON) of the hydrocarbon product of the alkylation reaction. The method includes determining an alkylation reaction temperature value, determining the actual formulation of the liquid onium poly(hydrogen fluoride) composition, calculating a target concentration value of the onium in the composition using an equation disclosed herein and adjusting the actual concentration value to approximate the target concentration value. By utilizing this aspect of the present invention, the RON of the hydrocarbon product is adjusted to maintain the RON of the hydrocarbon product.

BRIEF DESCRIPTION OF THE DRAWINGS

These and other features of the present invention are more fully set forth in the following description of illustrative embodiments of the invention. The description is presented with reference to the accompanying drawings in which.

DESCRIPTION OF ILLUSTRATIVE EMBODIMENTS

Figure 1:
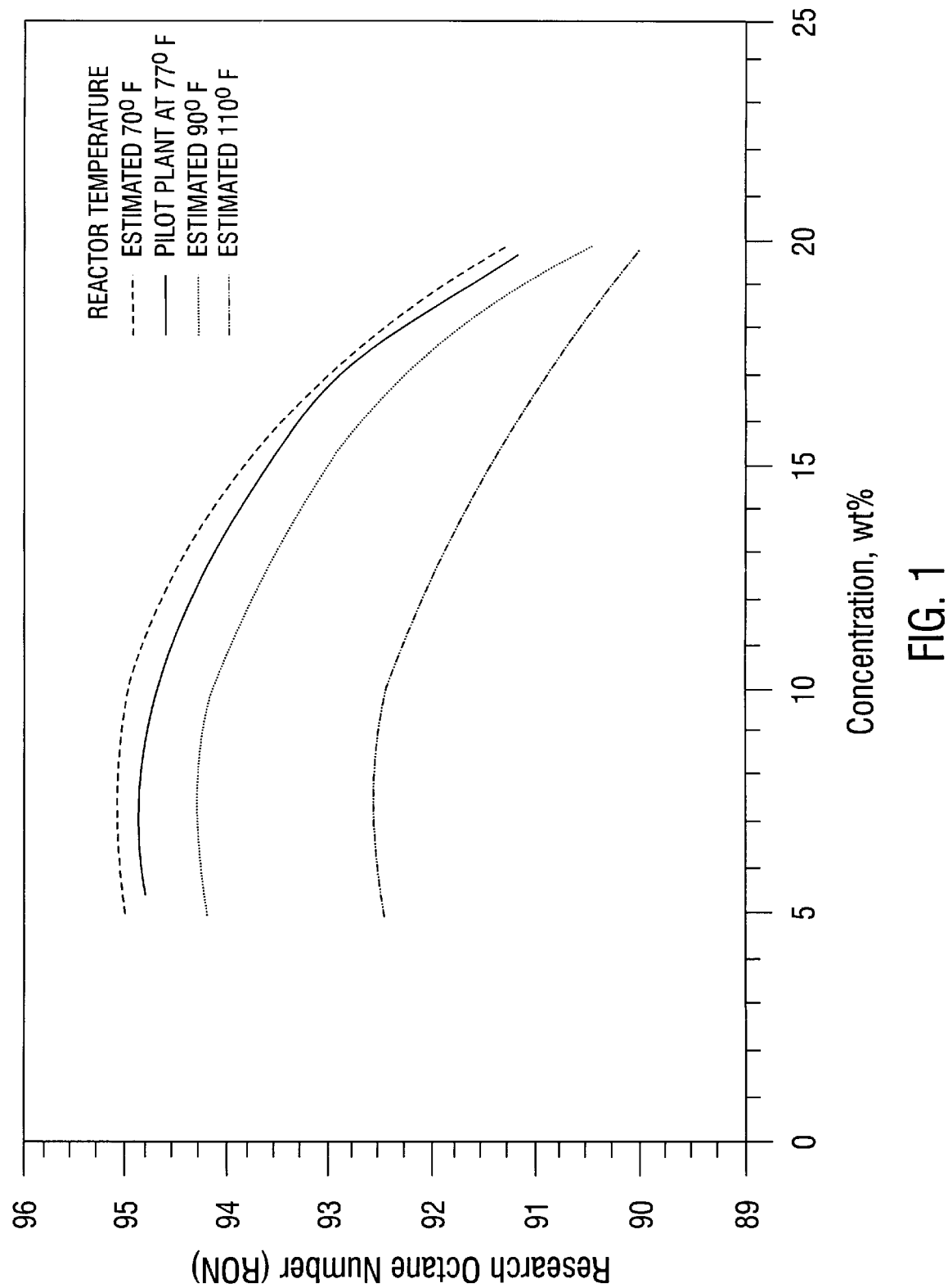
FIG. 1 is a graph of Research Octane Number (RON) versus pyridine concentration (wt %).

The present invention is generally directed to a method of regulating the formulation of a liquid onium poly(hydrogen fluoride) (hereafter referred to as "LOPHF") composition utilized in a hydrogen fluoride (hereafter referred to as "HF") catalyzed alkylation reaction. As the term is used herein, "onium" is used as a generic term for compounds selected from the group including ammonium, methylamines, ethylamines, propylamines, butylamines, pentylamines, pyridine, picoline, melamine, hexamethylene-tetramine and the like which form a LOPHF composition when mixed with anhydrous HF. In one embodiment, it has been found that a relationship exists between the level of total airborne hydrogen fluoride reduction and the concentration of the onium in the LOPHF utilized in the alkylation reaction. In another embodiment, it has been found that a relationship exists between the level of research octane number (RON) of the hydrocarbon product of the alkylation reaction and the concentration of the onium in the LOPHF utilized in the alkylation reaction. Both relationships are affected by other variables and factors, such as alkylation reaction temperature, reaction pressure, ambient temperature and so forth. One aspect of either embodiment is the ability to carefully regulate the formulation of the LOPHF composition based on either the level of safety desired, or the level of RON desired or both depending on the reaction conditions and the meteorological conditions at the reactor site.

The alkylation reaction is typically carried out between an isoparaffin and a monoolefin in the presence of an alkylation catalyst. Generally the isoparaffin is typically a $C_4$ to $C_{12}$ isoparaffin and the monoolefin is typically a $C_2$ to $C_{12}$ monoolefin. A preferred isoparaffin may be isobutane, although isopentane may also used. Common monoolefins include propylene, isobutylene, 1-butene, 2-butene, pentylenes and mixtures thereof. A preferred monoolefin may be a mixture of $C_4$ olefins which typically includes 1-butene, 2-butene and isobutene. This $C_4$ olefin mixture may be one fraction from a fluid catalytic cracking process, which may include about 25 vol % 1-butene, about 45 vol % 2-butene and about 30 vol % isobutylene. Diolefins or higher functionality olefins should be avoided in the reaction because these olefins alkylate at each double bond, forming polymers which are not useful in gasoline blends. A substantial molar excess of isoparaffin to olefin may be employed in a typical alkylation reaction so as to provide an isoparaffin/olefin feed ratio in excess of about 1/1, generally 4/1 to 70/1 and preferably 5/1 to about 20/1.

The alkylation catalyst typically is a strong mineral acid in liquid form and for the purposes of the present disclosure hydrogen fluoride is preferred. Hydrogen fluoride is often referred to as anhydrous hydrofluoric acid or, as it is herein, simply by its molecular symbol HF. The HF used as an alkylation catalyst typically contains no more that about 5% by weight of water. One of ordinary skill in the art should appreciate that anhydrous HF is a very strong acid and as such serves as a Lewis acid catalyst in the alkylation reaction. Further one skilled in the art should appreciate that HF has a very strong corrosive effect on human and animal tissue and therefore poses a significant hazard to the surrounding environment should an accidental release occur.

The alkylation reaction may be carried out at pressures varying from atmospheric to as high as 1000 psia (68 ATM) or higher, preferably about 125 to 220 psia (8.5 to 15 ATM) and at residence times of 20 seconds to 5 minutes. The pressure is selected in cooperation with the temperature to maintain the hydrocarbon reactants in liquid phase and generally at an alkylation reaction temperature ranging from −40° F. (−24° C.) to about 150° F. (66° C.). In the preferred reaction of isobutane with a $C_4$ monoolefin the reaction temperature is between about 60° F. (15° C.) and about 100° F. (38° C.) and most preferably about 90° F. (32° C.).

U.S. Pat. No. 5,073,674 to G. A. Olah, the contents of which are hereby incorporated herein by reference, generally discloses a HF catalyzed alkylation reaction using a variety of liquid onium poly(hydrogen fluoride) (herein referred to as LOPHF) compositions. Suitable LOPHF compositions are those of made from anhydrous HF and onium compounds selected from the group including ammonium, methylamines, ethylamines, propylamines, butylamines, pentylamines, pyridine, picoline, melamine, hexamethylene-tetramine and the like with the onium component being present in an amount between 5% and 30% by weight. The liquid onium poly(hydrogen fluoride) compositions are formed spontaneously at a temperature of −20° C. to 70° C. and a pressure of atmospheric to 14 atmospheres by adding a LOPHF composition forming onium to anhydrous hydrogen fluoride. The reference suggests that these compositions will display less volatility at alkylation reaction temperatures than anhydrous HF because of their low, below 35° to 50° C., vapor pressure.

The present invention is an improvement over the Olah technology and is based on empirically derived equations which calculate target concentration values of onium in the LOPHF complex that will maximize safety, the RON value of the hydrocarbon product or both. These equations take into account the alkylation reaction conditions and the atmospheric conditions at the reactor site. Upon comparison of this target concentration value with the measured concentration value of onium in the LOPHF complex utilized in the alkylation reaction, one can adjust the actual concentration of onium to approximate the target concentration value. These adjustments may be made by either adding onium to increase the concentration or adding HF to decrease the concentration of onium. Thus one can carefully regulate the concentration of the onium present in the LOPHF composition utilized in the HF catalyzed alkylation reaction as the conditions of the reaction change or the meteorological conditions at the refinery site change while maintaining a predictable level of safety or RON value of hydrocarbon product or both.

In one embodiment an empirically derived equation is used to calculate a target concentration of onium for a given level of total airborne HF reduction. Thus a predictable and significantly reduced amount of HF becomes a hazardous aerosol should an accidental release occur. This is of great utility since one can predictably determine the concentration of onium needed to meet safety guidelines as conditions of either the alkylation reaction or the meteorological conditions at the reactor site change. This safety enhancement is possible because a predictable portion of any LOPHF complex remains in a liquid state or rapidly coalesces to form liquid droplets which fall to the ground around the alkylation unit. One of ordinary skill in the are should readily appreciate that it is much easier to mitigate a pool of liquid on the grounds of a refinery than it is to mitigate an airborne aerosol cloud of HF.

One method of quantitating the liquid coalescing phenomena known in the art is total airborne HF reduction. The total airborne HF reduction is measured relative to the % weight of a 100% HF release which would otherwise from an aerosol. The following equation is used to calculate the value of total airborne HF reduction:

$$H = 100(1 - w_0(1-c))$$

wherein: H is the total airborne HF reduction in weight %; $w_0$ is the weight fraction of HF in the released mixture; and c is the weight fraction of coalesced liquid collected. One skilled in the art should, upon careful examination of this equation, realize that low values of H (e.g. below 50) indicate that a majority of the HF remains airborne. Likewise, high values of H (e.g. above 50) indicate that a majority of HF does not remain airborne and forms a coalesced liquid.

A study of seventeen pyridine based liquid onium poly (hydrogen fluoride) compositions was conducted in a large scale experimental apparatus for measuring total airborne HF reduction at various ambient temperatures. The apparatus, constructed for this purpose, included an acid reservoir, release orifice, release chamber, recovered liquid weighing pan and instrumentation and is described in detail in the paper "Apparatus for Field Testing of HF Releases" K. W. Schatz, G. R. Jersey, M. K. Chalam and D. W. Johnson, AIChE Summer National Meeting, August, 1993, the contents of which are hereby incorporated herein by reference. In the present studies, a weighed amount of liquid onium poly(hydrogen fluoride) composition was released through an orifice of specified diameter into a 30,720 ft³ chamber. Coalesced liquid was collected in weighing pans and the total amount was weighed. Exemplary results are given in Table 1.

TABLE 1

| Liquid Onium Poly(HF) Composition | | | Orifice Temp. (K.) | Orifice Pressure (kPa) | Orifice Diameter (mm) | Ambient Temp. (K.) | Recovered Liquid (% weight) | Run Duration (sec.) | Calculated Value of H (% weight) |
|---|---|---|---|---|---|---|---|---|---|
| HF (% weight) | Pyridine (% weight) | Water (% weight) | | | | | | | |
| 100.000 | 0 | 0 | 305.480 | 689.350 | 6.350 | 297.678 | 2.93 | 266.0 | 2.93 |
| 86.468 | 11.128 | 2.404 | 312.540 | 681.876 | 3.175 | 300.818 | 29.09 | 2782.0 | 38.69 |
| 86.468 | 11.128 | 2.404 | 298.560 | 630.466 | 12.700 | 296.902 | 67.90 | 55.8 | 72.24 |
| 81.023 | 16.531 | 2.446 | 297.890 | 665.740 | 12.700 | 296.902 | 79.01 | 55.4 | 82.99 |
| 77.090 | 20.815 | 2.095 | 297.520 | 623.481 | 19.050 | 296.388 | 87.50 | 48.2 | 90.39 |
| 77.090 | 20.815 | 2.095 | 298.310 | 658.476 | 12.700 | 302.078 | 84.12 | 54.8 | 87.76 |
| 77.090 | 20.815 | 2.095 | 304.780 | 681.596 | 12.700 | 303.686 | 80.24 | 46.8 | 84.77 |
| 83.094 | 14.225 | 2.681 | 305.110 | 653.237 | 12.700 | 303.405 | 72.23 | 50.0 | 76.92 |
| 83.094 | 14.225 | 2.681 | 315.860 | 682.365 | 12.700 | 303.895 | 65.40 | 44.4 | 71.25 |
| 82.040 | 15.110 | 2.850 | 304.220 | 955.967 | 12.700 | 298.221 | 73.22 | 50.2 | 78.03 |
| 82.627 | 15.404 | 1.969 | 304.361 | 668.403 | 12.700 | 305.966 | 71.64 | 71.0 | 76.57 |
| 82.627 | 15.404 | 1.969 | 305.082 | 1612.916 | 12.700 | 308.751 | 64.91 | 75.4 | 71.01 |
| 80.710 | 17.613 | 1.677 | 304.755 | 667.824 | 12.700 | 309.405 | 71.55 | 176.5 | 77.04 |
| 80.710 | 17.613 | 1.677 | 305.200 | 351.832 | 12.700 | 309.306 | 76.97 | 87.0 | 81.41 |
| 77.302 | 20.329 | 2.369 | 304.509 | 681.925 | 6.350 | 306.288 | 75.06 | 242.5 | 80.72 |
| 81.441 | 16.137 | 2.422 | 305.708 | 676.853 | 12.700 | 313.373 | 71.39 | 60.4 | 76.70 |
| 81.226 | 16.494 | 2.280 | 302.982 | 753.406 | 12.700 | 311.484 | 68.70 | 87.8 | 74.58 |

From the data of the above studies an empirical equation has been derived to determine a target concentration value of onium in the LOPHF composition utilized in the alkylation reaction for a given total airborne HF reduction. The equation takes into account changes in the alkylation reaction temperature, the alkylation reaction pressure and the ambient temperature. The equation is:

$$C = a + bH + cT_r + dP + eT_a + fHT_r + gHP + hHT_a + iT_aP + jT_rT_a + kPT_a + lH^2 + mT_r^2 + nP^2 + to_a^2$$

wherein: C is the target concentration value of onium in mass fraction; H is the total airborne hydrogen fluoride reduction in weight percent; $T_a$ is the ambient temperature value in degrees Kelvin; $T_r$ is the alkylation reaction temperature value in degrees Kelvin; P is the alkylation reaction pressure value in kiloPascals; a=109.99073; b=−0.27626; c=−1.38790; d=−0.03703; e=0.81024; f=0.00283; g=0.00014; h=−0.00238; i=0.00014; j=−0.00094; k=−0.00005; l=0.00038; m=0.00130; n=1.5×10$^{-6}$; and, o=−0.00143.

Thus according to a first embodiment of the invention, a value of total airborne HF recovery is chosen based on quantitative risk assessment, dispersion modeling and regulatory requirements. A value of the ambient temperature is determined by either measuring the ambient temperature or looking up a value from a table of historical average ambient temperature values. The alkylation reaction conditions of temperature, pressure and concentration of onium in the LOPHF composition are also measured. With this information and using the above equation, a target concentration value of onium can be calculated which will give the desired total airborne HF recovery. By comparing the target concentration value of onium with the measured concentration of the onium in the LOPHF composition, the concentration of onium can be adjusted so as to approximate the target value. These adjustments may be done by either adding onium to increase the concentration of onium or adding HF to decrease the concentration of onium in the composition, which is then utilized in the alkylation reaction.

In another embodiment, an empirically derived equation is used to calculate a target concentration of onium for a given level of research octane number (RON) desired in the hydrocarbon alkylate product. Liquid onium poly(hydrogen fluoride) compositions were formulated consisting of pyridine and anhydrous HF. These LOPHF compositions were tested in a pilot plant for effectiveness in producing alkylate at a reaction temperature of 77° F. (25° C.). The RON of each alkylate produced was measured according to ASTM D-2699. The results are shown graphically in FIG. 1. and exemplary results are given below in Table 2.

TABLE 2

| Wt % Pyridine | RON (ASTM D-2699) |
|---|---|
| 5 | 94.8 |
| 10 | 94.8 |
| 15 | 93.7 |
| 20 | 91.1 |

Estimated values for Research Octane Number (RON) at reactor temperatures of 70° F. (21.1°), 90° F. (32.2° C.) and 110° F. (43.3° C.) are also plotted in FIG. 2. The estimated values of RON were interpolated and extrapolated from the pilot plant data at 77° F. is (25° C.) and published HF alkylation reaction data in the 80° F. (26.7° C.) to 100° F. (37.8° C.) range. Published data was taken from the following sources: A. Corma and A. Martinez, Chemistry Catalysts and Processes for Isoparaffin-Olefin Alkylation: Actual Situation and Future Trends., Catal. Rev.-Sci. Eng., 35(4), 483–570 (1993); G. T. Stevenin, Alkylation for Motor Fuels, Stanford Research Institute, February 1974; 1981, 1982, 1986—National Petroleum Refiners Association (NPRA) Question and Answer Session on Refining and Petrochemical Technology.

In some commercial hydrogen fluoride alkylation reactors, the reaction temperature varies dependently with the temperature of the cooling water supplied to moderate temperature. Cooling water temperature, in turn, varies dependently with the temperature of the ambient air passing through the associated cooling tower. In general, reaction temperature ranges between 60° F. (15.6° C.) and 120° F. (48.9° C.), typically between 80° F. (26.7° C.) and 100° F. (37.8° C.) as a result of ambient air temperature variation. It is known that alkylate quality improves as reaction temperature is reduced. Alkylate quality increases about one Research Octane Number (RON) per 19.8° F. (11° C.) to 27° F. (15° C.) reduction in reaction temperature.

From the above data, the following equation has been empirically determined:

$$C=a'+b'R+c'T_r+d'RT_r+e'R^2+fT_r^2$$

wherein C is the target concentration value of pyridine in mass fraction; R is the RON value of the hydrocarbon alkylate product; $T_r$ is the alkylation reaction temperature value in degrees Kelvin; a'=−84.11875056; b'=1.227443844; c'=0.196482957; d'=−0.001032704; e'=−0.005143374; and, f'=−0.000172411.

Accordingly in another embodiment of the invention, a value of RON is chosen; and, the alkylation reaction conditions of temperature, and concentration of onium in the LOPHF composition are measured. With this information and using the above equation, a target concentration value of onium in the LOPHF composition is calculated which will give the selected RON value in the product hydrocarbon. By knowing the target concentration value and the measured concentration of the onium in the LOPHF composition, the concentration of onium in the LOPHF is adjusted so as to approximate the target value. This may be done by either adding onium to increase the concentration value of onium in the LOPHF composition or adding HF to decrease the concentration of onium in the LOPHF composition which is then utilized in the alkylation reaction.

While the compositions and methods of this invention have been described in terms of preferred embodiments, it will be apparent to those of skill in the art that variations may be applied to the process described herein without departing from the concept, spirit and scope of the invention. All such similar substitutes and modifications apparent to those skilled in the art are deemed to be within the spirit, scope and concept of the invention as it is set out in the following claims.

What is claimed is:

1. A method of regulating the concentration of onium in a liquid onium poly(hydrogen fluoride) composition utilized in a hydrogen fluoride catalyzed alkylation reaction for a given level of total airborne hydrogen fluoride reduction comprising:

determining an ambient temperature value;

measuring an alkylation reaction temperature value;

measuring an alkylation reaction pressure value;

measuring a concentration value of the onium in the liquid onium poly(hydrogen fluoride) composition utilized in the alkylation reaction;

calculating a target concentration value of onium using the following equation $$C=a+bH+cT_r+dP+eT_a+fHT_r+gHP+hHT_a+iT_aP+jT_rT_a+kPT_a+lH^2+mT_r^2+nP^2+oT_a^2$$

wherein: C is the target concentration value of onium in mass fraction; H is the total airborne hydrogen fluoride reduction in weight percent; $T_a$ is the ambient temperature value in degrees Kelvin; $T_r$ is the alkylation reaction temperature value in degrees Kelvin; P is the alkylation reaction pressure value in kiloPascals; a=109.99073; b=−0.27626; c=−1.38790; d=−0.03703; e=0.81024; f=0.00283; g=0.00014; h=−0.00238; i=0.00014; j=−0.00094; k=−0.00005; l=0.00038; m=0.00130; n=1.5×10$^{-6}$; and, o=−0.00143, and adjusting the concentration of onium in the liquid onium poly(hydrogen fluoride) composition used in the alkylation reaction to approximate the target concentration value.

2. The method of claim 1 wherein the ambient temperature value is determined by measuring the ambient temperature.

3. The method of claim 1 wherein the ambient temperature value is determined by looking the value up in a table of historic average ambient temperature values.

4. The method of claim 1 wherein the onium is selected from the group consisting of ammonia, methylamines, ethylamines, propylamines, butylamines, pentylamines, pyridine, picoline, melamine, and hexamethylene-tetramine.

5. The method of claim 4 wherein the onium is pyridine.

6. The method of claim 5 wherein the given level of total airborne hydrogen fluoride reduction has a value of 20% weight to 95% weight.

7. The method of claim 6 wherein the given level of total airborne hydrogen fluoride reduction has a value of 50% weight to 80% weight.

8. The method of claim 1 wherein the ambient temperature value and the alkylation reaction temperature have approximately the same value.

9. A method of regulating the concentration of onium in a liquid onium poly(hydrogen fluoride) composition utilized in a hydrogen fluoride catalyzed alkylation reaction for a given value of RON in the hydrocarbon product comprising:

measuring an alkylation reactor temperature value;

measuring a concentration value of the onium in the liquid onium poly(hydrogen fluoride) composition utilized in the alkylation reaction;

calculating a target value of concentration of the onium in the liquid onium poly(hydrogen fluoride) composition utilized in the alkylation reaction using the equation $$C=a'+b'R+c'T_r+d'RT_r+e'R^2+fT_r^2$$

wherein C is the target concentration value of onium in mass fraction; R is the RON value of the hydrocarbon alkylate product; $T_r$ is the alkylation reaction temperature value; a'=−84.11875056; b'=1.227443844; c'=0.196482957; d'=−0.001032704; e'=−0.005143374; f'=−0.000172411; and, adjusting the concentration value of onium in the liquid onium poly(hydrogen fluoride) composition utilized in the alkylation reaction to approximate the target value.

10. The method of claim 9 wherein the onium is selected from the group consisting of ammonia, methylamines, ethylamines, propylamines, butylamines, pentylamines, pyridine, picoline, melamine, and hexamethylene-tetramine.

11. The method of claim 10 wherein the onium is pyridine.

12. The method of claim 11 wherein the given value of RON in the hydrocarbon product resulting from the alkylation reaction has a value of 85 to 100.

13. The method of claim 12 wherein the given value of RON in the hydrocarbon product resulting from the alkylation reaction has a value of 90 to 95.

14. A method of regulating the concentration of pyridine in a liquid pyridinium poly(hydrogen fluoride) composition utilized in a hydrogen fluoride catalyzed alkylation reaction for a given level of total airborne hydrogen fluoride reduction comprising:

determining an ambient temperature value;

measuring an alkylation reaction temperature value;

measuring an alkylation reaction pressure value;

measuring a concentration value of the pyridine in the liquid pyridinium poly(hydrogen fluoride) composition utilized in the alkylation reaction;

calculating a target concentration value of pyridine using the following equation $$C=a+bH+cT_r+dP+eT_a+fHT_r+gHP+hHT_a+iT_aP+jT_rT_a+kPT_a+lH^2+mT_r^2+nP^2+oT_a^2$$

wherein: C is the target concentration value of pyridine in mass fraction; H is the total airborne hydrogen fluoride reduction in weight percent; $T_a$ is the ambient temperature value in degrees Kelvin; $T_r$ is the alkylation reaction temperature value in degrees Kelvin; P is the alkylation reaction pressure value in kiloPascals; a=109.99073; b=−0.27626; c=−1.38790; d=−0.03703; e=0.81024; f=0.00283; g=0.00014; h=−0.00238; i=0.00014; j=−0.00094; k=−0.00005; l=0.00038; m=0.00130; n=1.5×10$^{-6}$; and, o=−0.00143 comparing the target concentration value with the measured concentration value and, adjusting the concentration of pyridine in the liquid pyridinium poly(hydrogen fluoride) composition used in the alkylation reaction to approximate the target concentration value.

15. A method of regulating the concentration of pyridine in a liquid pyridinium poly(hydrogen fluoride) composition utilized in a hydrogen fluoride catalyzed alkylation reaction for a given value of RON in the hydrocarbon product comprising:

measuring an alkylation reactor temperature value;

measuring a concentration value of the pyridine in the liquid pyridinium poly(hydrogen fluoride) composition utilized in the alkylation reaction;

calculating a target value of concentration of the pyridine in the liquid pyridinium poly(hydrogen fluoride) composition utilized in the alkylation reaction using the equation $$C = a' + b'R + c'T_r + d'RT_r + e'R^2 + f'T_r^2$$

wherein C is the target concentration value of pyridine in mass fraction; R is the RON value of the hydrocarbon alkylate product; $T_r$ is the alkylation reaction temperature value in degrees Kelvin; a'=−84.11875056; b'=1.227443844; c'=0.196482957; d'=−0.001032704; e'=−0.005143374; f'=−0.000172411; and, adjusting the concentration value of pyridine in the liquid pyridinium poly(hydrogen fluoride) composition utilized in the alkylation reaction to approximate the target value.

* * * * *

UNITED STATES PATENT AND TRADEMARK OFFICE
CERTIFICATE OF CORRECTION

PATENT NO.    : 5,859,305

DATED         : January 12, 1999

INVENTOR(S)   : Kenneth Roy Comey, III et al.

It is certified that error appears in the above-identified patent and that said Letters Patent is hereby corrected as shown below:

At Col. 5, line 33, please delete "$to_a^2$" and replace it with --$oT_a^2$--.

Signed and Sealed this

Twenty-seventh Day of July, 1999

Attest:

Q. TODD DICKINSON

*Attesting Officer*     *Acting Commissioner of Patents and Trademarks*

UNITED STATES PATENT AND TRADEMARK OFFICE
CERTIFICATE OF CORRECTION

PATENT NO.    : 5,859,305
DATED         : January 12, 1999
INVENTOR(S)   : Kenneth Roy Comey, III et al.

It is certified that error appears in the above-identified patent and that said Letters Patent is hereby corrected as shown below:   On the title page: Item

[75] Inventors, please add --Lee K. Gilmer, Houston--

Signed and Sealed this

Ninth Day of November, 1999

Attest:

Q. TODD DICKINSON

*Attesting Officer*    Acting Commissioner of Patents and Trademarks